United States Patent [19]

Ihara et al.

[11] Patent Number: 5,530,084
[45] Date of Patent: Jun. 25, 1996

[54] ORGANO(POLY)SILOXANE MODIFIED WITH PHOSPHORIC ESTER AND PROCESS FOR PRODUCING THE SAME

[75] Inventors: Takeshi Ihara, Wakayama; Shinji Yano, Naga-gun; Katsumi Kita, Izumisano; Yoshiaki Fujikura, Utsunomiya, all of Japan

[73] Assignee: Kao Corporation, Tokyo, Japan

[21] Appl. No.: 392,738

[22] PCT Filed: Sep. 9, 1993

[86] PCT No.: PCT/JP93/01279

§ 371 Date: Mar. 6, 1995

§ 102(e) Date: Mar. 6, 1995

[87] PCT Pub. No.: WO94/05720

PCT Pub. Date: Mar. 17, 1994

[30] Foreign Application Priority Data

Sep. 9, 1992 [JP] Japan .................................. 4-240689

[51] Int. Cl.$^6$ .................................................. C08G 77/04
[52] U.S. Cl. .................... 528/33; 528/30; 525/474
[58] Field of Search .................. 528/33, 30; 525/474

[56] References Cited

U.S. PATENT DOCUMENTS 5,070,171  12/1991  O'Lenick, Jr. .......................... 528/33
5,149,765  9/1992  O'Lenick, Jr. .
5,237,035  8/1993  O'Lenick, Jr. et al. .................. 528/33

FOREIGN PATENT DOCUMENTS 0164535  12/1985  European Pat. Off. .
0292760  11/1988  European Pat. Off. .

*Primary Examiner*—Melvyn I. Marquis
*Attorney, Agent, or Firm*—Oblon, Spivak, McClelland, Maier & Neustadt

[57] ABSTRACT

The present invention relates to organo(poly)siloxanes modified by phosphates (including alkali metal salts thereof or the like) suitable as a component of cosmetics, and to a process for the manufacture of organo(poly)siloxanes modified by phosphates (including alkali metal salts thereof or the like) comprising reacting an organo(poly)siloxane having a group HO—$(R^4O)_q$—$R^5$—$OR^6)_r$— in its molecular chain, wherein $R^4$–$R^6$ are alkylene groups, with an oxyhalogenated phosphorus; and further reacting it with an alkaline solution. These phosphate-modified organo(poly)siloxanes can stably emulsify silicone oils commonly used as cosmetic raw materials, irrespective of temperatures, and exhibit excellent compatibility with polar components and good foaming capability, so that they are suitable as a component of cosmetics such as skin cosmetics, skin detergents, hair cosmetics, hair detergents, and the like.

17 Claims, 4 Drawing Sheets

ORGANO(POLY)SILOXANE MODIFIED WITH PHOSPHORIC ESTER AND PROCESS FOR PRODUCING THE SAME

DESCRIPTION

1. Field of the Invention

The present invention relates to phosphate-modified organo(poly)siloxanes which are useful as a component of toiletries (perfumes and cosmetics), and further to a process for producing phosphate-modified organo(poly)siloxanes, which is suitable for the manufacture of said organo(poly)siloxanes whose terminals are modified by phosphates.

2. Description of the Background Art

Organopolysiloxanes (silicone oils) are commonly used as a component of hair-finishing agents, as well as a component of various cosmetics, because they impart no greasy feeling and are highly safe. Recently, in addition to the conventional use as a component of cosmetics, application of these compounds as a component of various toiletry items including perfumes has been studied. In order to conform to these new applications, further improvements in the characteristics of organopolysiloxanes, such as compatibility, resistance to chemicals, solubility in water, lubricity, and the like, are required.

To satisfy these requirements, various organopolysiloxanes modified by introducing different functional groups, for example, amino-modified, epoxy-modified, carboxylic acid-modified, mercapto-modified, alcohol-modified, polyether-modified, fluoroalkyl-modified, alkyl-modified, ester-modified, and alkoxy-modified organopolysiloxanes have been studied and developed.

On the other hand, phosphoric esters of organic hydroxy compounds (including alkali metal salts thereof and the like) are known to have an excellent surface activity. In particular, phosphoric monoesters are known to exhibit much higher surface activity than phosphoric diesters. For example, alkali metal salts or alkanol amine salts of phosphoric monoester of a long chain alkyl alcohol are water-soluble, and their aqueous solutions exhibit strong foaming capability and detergency, while the salts of phosphoric diester are scarcely soluble in water, exhibit almost no foaming capability, and moreover cause defoaming activity.

As compounds which have both the characteristics of the above-described phosphoric esters of organic hydroxy compounds and the aforementioned modified organopolysiloxanes, U.S. Pat. No. 5,070,171 and U.S. Pat. No. 5,093,452 disclosed certain compounds in which salts of phosphoric ester are introduced to the silicon atoms of the siloxane bonds in its main chain (excluding the both ends) via a lower alkylene group (limited only to the group having 3 carbon atoms) or polyalkyleneoxy groups, as connective groups, using 115% phosphoric acid, phosphorus pentoxide, or polyphosphoric acid.

However, the above-described conventional modified organopolysiloxanes are not necessarily satisfactory as a component of toiletries. Polyether-modified organopolysiloxanes, for example, have a problem in that they have poor heat stability in emulsion systems due to the cloud point phenomenon which is characteristic to the nonionic surface active agents comprising polyether bonds, rendering them unsuitable for practical use. The compounds disclosed in U.S. Pat. No. 5,070,171 and U.S. Pat. No. 5,093,452 are not satisfactory as an ingredient of toiletries, since they have only a small phosphorylation rate because of defects in the preparation method and are composed of a mixture with a small content of monoesters which are useful as surfactants. In addition, since the alkylene groups are of short chain, the overall hydrophilic-hydrophobic characteristic is imbalanced, giving rise to weak surface activity. They are thus not satisfactory as ingredients to be incorporated into toiletries.

Accordingly, an object of the present invention is to provide a modified organo(poly)siloxane exhibiting excellent compatibility, emulsifying capability, foaming capability, and the like, which is suitable for use as an ingredient of toiletries. Another object is to provide a novel process for the manufacture of a modified organo(poly)siloxane, which can be applied to the preparation of said modified organo(poly)siloxanes of the present invention.

DISCLOSURE OF THE INVENTION

The present invention relates to a phosphate-modified organo(poly)siloxane represented by the following formula (1):

wherein R, which may be the same or different, indicates an alkyl group or an alkoxy group having 1 to 22 carbon atoms, or a group represented by the following formula (2) or (3):

(wherein $R^4$ and $R^6$ represent an alkylene group having 2 to 4 carbon atoms, $R^5$ indicates a linear or branched alkylene group having 4 to 50 carbon atoms, which may or may not contain hydroxy groups, $M^1$ and $M^2$ indicate a hydrogen atom, an alkali metal, an ammonium group, an alkyl amine or an alkanol amine, q is a number of 0 to 200, r is 0 or 1); $R^1$ and $R^2$ designate a group represented by the following formula (2') or (3'), (wherein $R^4$ and $R^6$ designate the same groups as defined above, $R^{5'}$ indicates a linear or branched alkylene group having 1 to 50 carbon atoms, which may or may not contain hydroxy groups, q, r, $M^1$ and $M^2$ are the same as defined previously), or an alkyl group or an alkoxy group having 1 to 22 carbon atoms, provided that at least one of $R^1$, $R^2$ and R represents the group indicated by the formula (2) or (2'); and n indicates a number of 0 to 1,000.

Further, the present invention relates to a process for the manufacture of an organo(poly)siloxane having at least one group represented by the following formula:

wherein $R^4$, $R^{5'}$, $R^6$, $M^1$, $M^2$, q and r are the same as defined previously, as a group bonded to the silicon atoms in the molecular chain, which comprises reacting an alcohol-modified organo(poly)siloxane having at least one group represented by formula HO—$(R^4O)_q$—$R^{5'}$—$OR^6)_r$, wherein $R^4$, $R^{5'}$, $R^6$, q and r are the same as defined previously, as a group bonded to the silicon atoms in the molecular chain, with an oxyhalogenated phosphorus, and hydrolyzing the bonds between the phosphorus and the halogen.

The above-described organo(poly)siloxanes modified by phosphates excel in foaming capability and emulsifying capability, as well as heat stability in emulsion systems and compatibility with other ionic components. Furthermore, the above-described process is useful in that it can be applied to the manufacture of other phosphate-modified organo(poly)siloxanes.

BEST MODES FOR CARRYING OUT THE INVENTION

In the present invention, the term "organo(poly)siloxanes" means various organopolysiloxanes from high molecular weight organopolysiloxanes to low molecular weight organosiloxanes. "Phosphate" as used in "modified by phosphate" or "phosphate-modified" in the present invention includes phosphates themselves and the above-mentioned alkali metal salts, ammonium salts, alkyl amine salts or alkanol amine salts of a phosphate.

R in formula (1) represents an alkyl group or an alkoxy group having 1 to 22 carbon atoms, or a group represented by formula (2) or (3). Among these preferred groups are alkyl or alkoxy groups having 1 to 6 carbon atoms or groups represented by formula (2) wherein $R^5$ is an alkylene group having 4 to 15 carbon atoms, with methylene group and groups represented by formula (2) wherein $R^5$ is an alkylene group having 6 to 12 carbon atoms being particularly preferred. Also, even though n in formula (1) designates a number of 0 to 1,000, a range of 0 to 100, particularly 0 to 50, or more particularly 0 to 10, is preferred when the compounds are used as ingredients of toiletries. In formula (2), (2'), (3) or (3'), preferable $R^5$ or $R^{5'}$ are those having 4 to 15 carbon atoms, particularly those having 6 to 12 carbon atoms; a preferable value for q is 0 to 15; and a preferable value for r is 0. For $M^1$ and $M^2$ in formula (2), a hydrogen atom or an alkali metal is particularly preferred.

Given as examples of oxyhalogenated phosphorus compounds used in the present invention are phosphorus oxychloride, phosphorus oxybromide, and the like. Of these, phosphorus oxychloride is particularly preferred.

The phosphate-modified organo(poly)siloxanes, including the compounds represented by the above formula (1), are prepared in the following manner. An organo(poly)siloxane having groups represented by formula (2) or (2'), as a group bonded to the silicon atoms in its molecular chain, can be prepared by reacting an alcohol-modified organo(poly)siloxane having at least one group represented by formula (3) or (3'), as a group bonded to the silicon atoms in the molecular chain, with an oxyhalogenated phosphorus compound, followed by hydrolyzing the bond between the phosphorus and the halogen.

Now, the process of the present invention will be discussed on each manufacturing step. First, an alcohol-modified organo(poly)siloxane having at least one group represented by formula (3) or (3'), as a group bonded to the silicon atoms in the molecular chain (hereinafter referred to as "alcohol-modified organo(poly)siloxane"), is reacted with an oxyhalogenated phosphorus compound in the presence or absence of a solvent.

Any alcohol-modified organo(poly)siloxanes can be used in the present invention, so long as the same have at least one group represented by (3) or (3') bonded to the silicon atom in the molecular chain, with no restriction being imposed on the position of the bond. Any type of structures, named generically as branched type, both-end type, one-end type, T-structure type, and the like, depending on the linked position of the specified groups, can therefore be used. The compounds represented by the following formulas can be given as examples of these alcohol-modified organo(poly)siloxanes.

wherein j, k, l and m designate a number of 0 to 1,000.

Although alcohol-modified organo(poly)siloxanes prepared by known methods can be used, commercial products may also be used as they are. Given as examples of such commercial products are X-22-170, X-22-170A, X-22-170B, X-22-170D, X-22-160AS, KF6001, KF6002, KF6003, X-22-176B, X-22-176D, X-22-4015 (manufactured by Shin-Etsu Chemical Co., Ltd.); TSL-9105, TSF4705, TSF4751, XF42-220, XF42-811, XF42-831 (manufactured by Toshiba Silicone Co., Ltd.); and PS197, PX101 (manufactured by Chisso Corp.).

There are no particular restrictions to the reaction method of alcohol-modified organo(poly)siloxane and oxyhalogenated phosphorus. For example, it is possible to apply a method in which each compound is dissolved in an appropriate solvent and the solutions are mixed together to proceed the reaction.

Examples of the solvents used for dissolving alcohol-modified organo(poly)siloxanes include tetrahydrofuran, methylene chloride, toluene, diethyl ether, and the like. The amount of the solvent to be used here is preferably less than 10-fold, more preferably less than 3-fold, of the weight of the alcohol-modified organo(poly)siloxane. Examples of the solvents used for dissolving an oxyhalogenated phosphorus compound include tetrahydrofuran, methylene chloride, toluene, ether, and the like. The amount of the solvent to be used here is preferably less than 20-fold, more preferably less than 10-fold, of the weight of the oxyhalogenated phosphorus compound.

Although the mixing ratio of an alcohol-modified organo(poly)siloxane and an oxyhalogenated phosphorus compound is not particularly restricted, it is preferable to mix 0.5 to 2, or more preferably 0.9 to 1.5, equivalent of oxyhalogenated phosphorus to 1 equivalent of hydroxyl group contained in the alcohol-modified organo(poly)siloxane.

Although the mixing method of an alcohol-modified organo(poly)siloxane and an oxyhalogenated phosphorus compound is not particularly restricted, it is possible to apply a method, for example, in which an alcohol-modified organo(poly)siloxane solution is added dropwise to an oxyhalogenated phosphorus solution, while stirring if required.

In this instance, the method of the dropwise addition is not particularly limited. Any methods, for example, dripping the total volume at a time, dripping portions at appropriate intervals, or dripping little by little in portions, can be applied. The temperature in the reaction system at the time of dripping is preferably −50° to 10° C., with a more preferable temperature range being −30° to 0° C. Upon completion of the reaction, it is preferable, as needed, to perform an aging operation for 1 to 5 hours within the aforementioned temperature range. For the purpose of neutralization of the by-produced hydrochloric acid, it is possible to have a tertiary amine such as triethylamine, tributylamine, pyridine, N-methylmorpholine, and the like coexist in the reaction system.

Next, in order to hydrolyze the bonds between phosphorus and halogen in the reaction product prepared in the preceding step, an alkaline solution may be added, for example, by applying a similar dripping method as described above, and reacted.

The alkaline solution used here includes a solution of sodium hydroxide, potassium hydroxide, ammonium, alkyl amine, alkanol amine, or the like. Among these, particularly preferred are a solution of sodium hydroxide and a solution of potassium hydroxide. The concentration of the alkaline solution is not particularly limited. It can be appropriately adjusted taking the concentrations of the alcohol-modified organo(poly)siloxane and the oxyhalogenated phosphorus into consideration. In addition, the temperature of the reaction system is preferably maintained at the same temperature range as described previously, and the reaction time is preferably 1 to 15 hours.

After completing the reactions in this manner, the phosphate-modified organo(poly)siloxane produced is separated from the reaction system. A further purification operation may be additionally performed on the phosphate-modified organo(poly)siloxanes thus produced, as needed. This purification operation is not particularly limited and can be carried out, for example, by the following methods. 1) A method comprising adding water and a non-hydrophilic solvent such as butanol, toluene, etc., and if required, further adding a demulsifier such as ethanol, 2-propanol, or the like, to the reaction solution; stirring the mixture; allowing the mixture to stand still for phase separation; and removing the water layer containing extra phosphates and by-produced inorganic and organic salts. 2) A method of removing the solvent from the reaction mixture by evaporation; then washing the residue with water to remove the extra phosphates and the like, or dissolving the residue into a solvent such as ethanol, propanol, butanol, toluene, etc. to filtrate the precipitated extra phosphates and the like. 3) A method of adding a hydrophilic solvent such as ethanol, acetone, etc. to the separated water layer to precipitate the target compound. This last-mentioned method is applicable to the case where the phosphate-modified organo(poly)siloxanes produced are undissolvable in an organic solvent.

EXAMPLES

The present invention will be described in more detail by way of examples which are not intended to be limiting the present invention.

Example 1

A solution of 820 mg of phosphorus oxychloride dissolved in 3 g of tetrahydrofuran was cooled to −30° C. To this solution, a solution of 10 g of one-end type alcohol-modified dimethylpolysiloxane represented by the following formula, (trademark: X-22-170A, alcohol equivalent 31, manufactured by Shin-Etsu Chemical Co., Ltd.) and 540 mg of triethylamine dissolved in 10 g of tetrahydrofuran was added dropwise over 20 minutes, and reacted. The reaction mixture was left for aging for 4 hours, while maintaining the temperature below −20° C. Then, a solution of 1.0 g of sodium hydroxide dissolved in 3 g of ion-exchanged water was added dropwise to the reaction mixture over 20 minutes. The stirring was continued for 12 hours at 0° C. and the reaction was terminated. 50 g of ion-exchanged water was added to the reaction mixture, followed by further addition of a mixed solvent of diethyl ether and ethanol to extract the reaction product. The organic layer was washed with ion-exchanged water and the water layer was removed. 10 g of phosphate-modified dimethylpolysiloxane of the present invention was obtained by removing the solvent by evaporation under a reduced pressure. This phosphate-modified dimethylpolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

This compound was analyzed by NMR and IR (neat method). The results of NMR analysis are given below and the IR spectrum is presented in FIG. 1.

Figure 1:
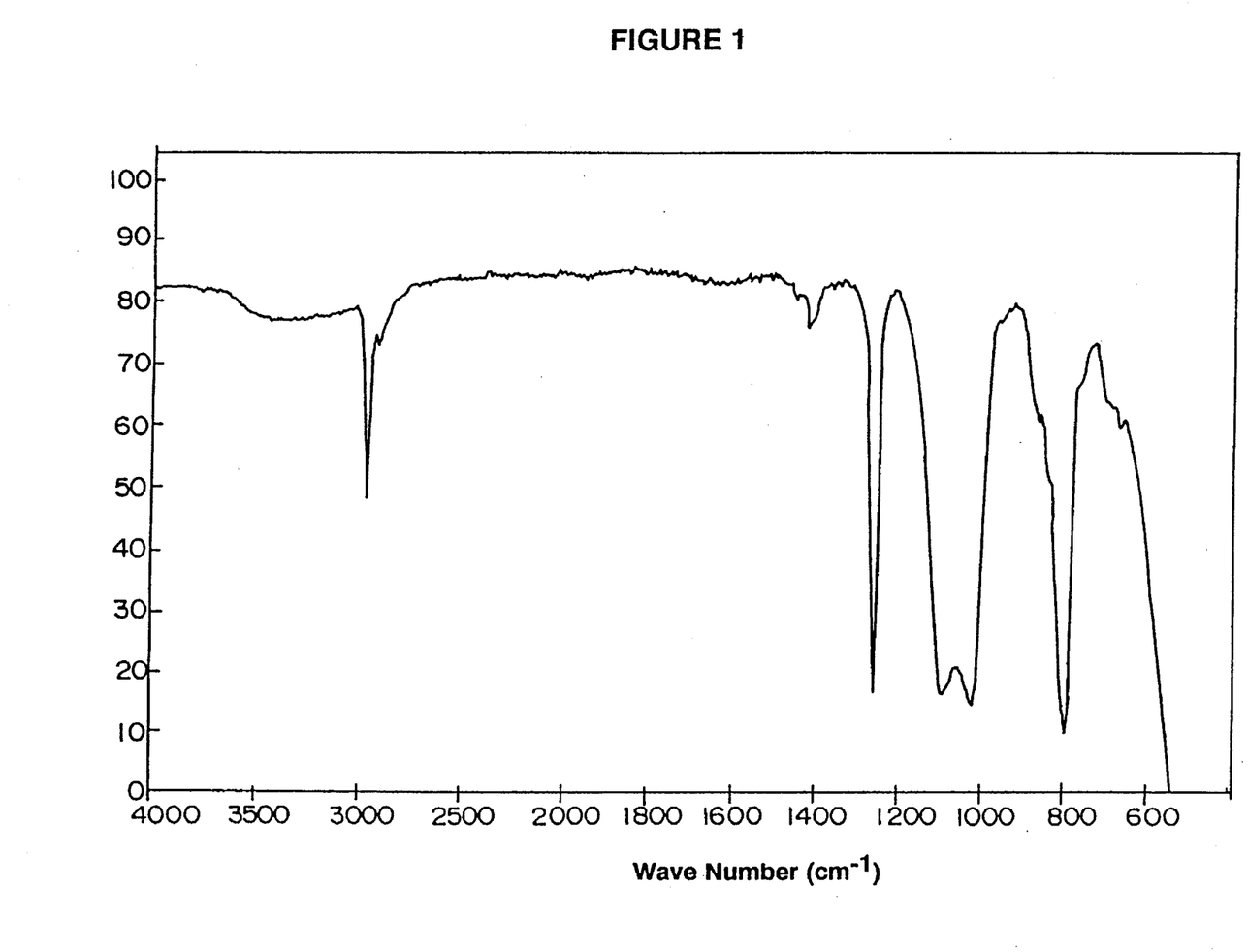
FIG. 1 is an IR spectrum of dimethylpolysiloxane prepared in Example 1.

$^{31}$P-NMR(CDCl$_3$); δ(ppm) 8.2

$^1$H-NMR (CDCl$_3$); δ(ppm) 0.1 (broad s, 147H, Si—CH$_3$), 0.5 (m, 2H, —O—Si—CH$_2$—CH$_2$—CH$_2$—O—), 1.6 (m, 2H, —O—Si—CH$_2$CH$_2$CH$_2$—O—), 3.4 (m, 2H, —CH$_2$—O—(CH$_2$)$_2$—O—P̄), 3.55 (m, 2H, —CH$_2$—O—C

$\underline{H_2}$—CH$_2$—O—P), 3.72, 3.91 (m, 2H, —C$\underline{H_2}$—O—P).

These analytical results confirmed that this phosphate-modified dimethylpolysiloxane has the structure defined by the following formula.

Example 2

A solution of 15.2 g of phosphorus oxychloride dissolved in 15 g of tetrahydrofuran was cooled to −30° C. To this solution, a solution of 50 g of both-end type alcohol-modified dimethylpolysiloxane represented by the following formula, (trademark: X-22-160AS, alcohol equivalent 112, manufactured by Shin-Etsu Chemical Co., Ltd.) and 10 g of triethylamine dissolved in 40 g of tetrahydrofuran was added dropwise over 40 minutes, and reacted. The reaction mixture was left for aging for 4 hours, while maintaining the temperature of the reaction system below −20° C. Then, a solution of 20.7 g of sodium hydroxide dissolved in 40 g of ion-exchanged water was added dropwise to the reaction mixture over 40 minutes. The stirring was continued for 12 hours at 0° C. and the reaction was completed. Then, after removing the solvent from the mixture by evaporation, 300 g of ion-exchanged water was added to the mixture and insoluble substances were removed by filtration. 100 ml of ethanol was added to the filtrate and solid substance formed was removed by filtration to obtain 52 g of phosphate-modified dimethylpolysiloxane of the present invention. This dimethylpolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

This compound was analyzed by NMR and IR (KBr method). The results of NMR analysis are given below and the IR spectrum is presented in FIG. 2.

Figure 2:
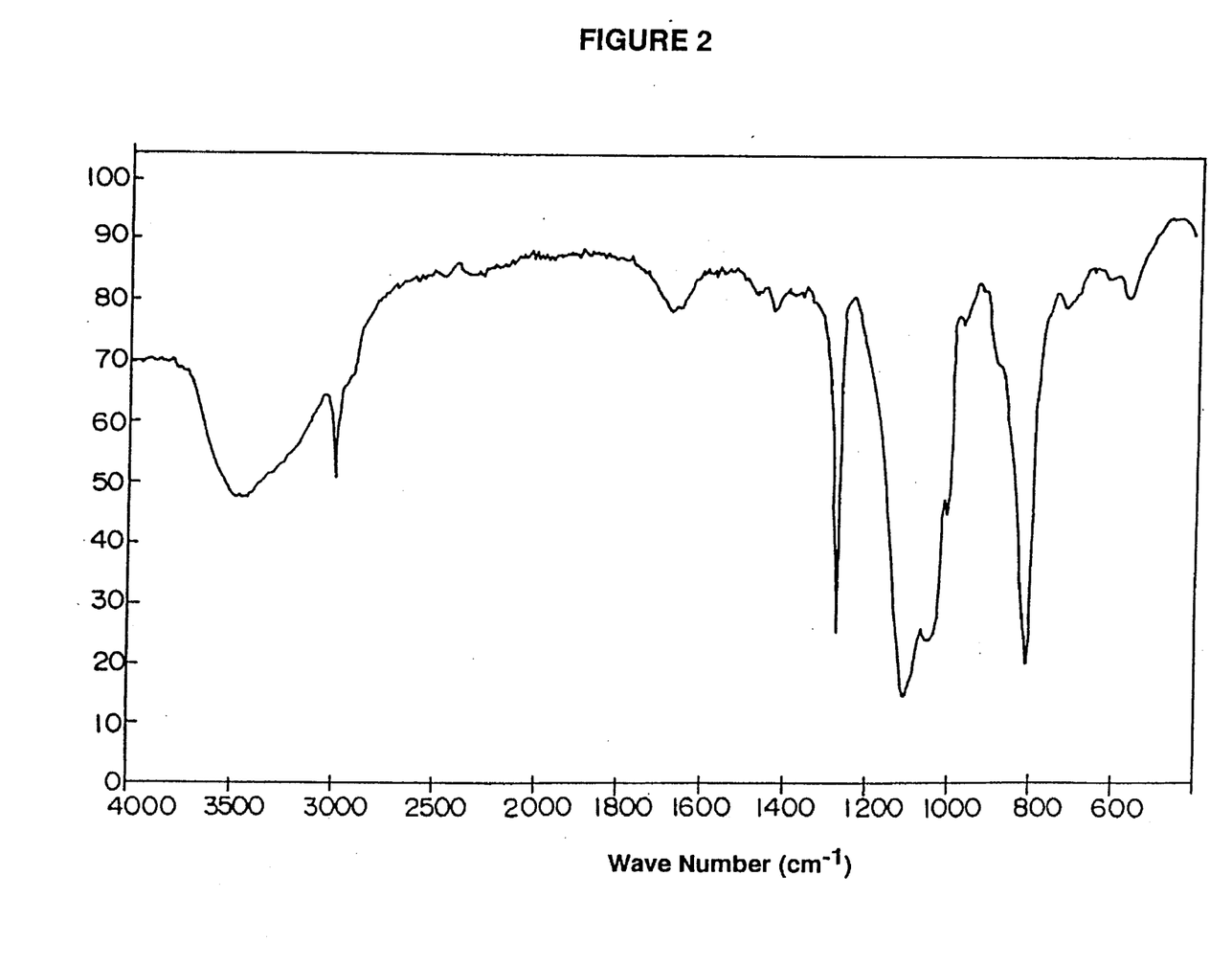
FIG. 2 is an IR spectrum of dimethylpolysiloxane prepared in Example 2.

$^{31}$P-NMR(CDCl$_3$); δ(ppm) 8.2

$^{1}$H-NMR (D$_2$O); δ(ppm) 0.1 (broad s, 66H, Si—CH$_3$), 0.52 (m, 4H, —O—Si—C$\underline{H_2}$—CH$_2$—), 1.55 (m, 4H, —O—Si—CH$_2$C$\underline{H_2}$CH$_2$—O—), 3.6 (m, 8H, —C$\underline{H_2}$—O—C$\underline{H_2}$—), 3.8 (m, 4H, —C$\underline{H_2}$—O—P—).

These analytical results confirmed that this phosphate-modified dimethylpolysiloxane has the structure defined by the following formula.

Example 3

A solution of 7.8 g of phosphorus oxychloride dissolved in 10 g of tetrahydrofuran was cooled to −30° C. To this solution, a solution of 80 g of both-end type alcohol-modified dimethylpolysiloxane represented by the following formula, (trademark: KF6002, alcohol equivalent 35, manufactured by Shin-Etsu Chemical Co., Ltd.) and 5.0 g of triethylamine dissolved in 30 g of tetrahydrofuran was added dropwise over 50 minutes, and reacted. The reaction mixture was left for aging for 4 hours, while maintaining the temperature of the reaction system below −20° C. Then, a solution of 10.6 g of sodium hydroxide dissolved in 20 g of ion-exchanged water was added dropwise to the reaction mixture over 40 minutes. The mixture was continuously stirred for 12 hours at 0° C. and the reaction was completed. Then, after removing the solvent by evaporation, the mixture was washed with ion-exchanged water (300 g×3). The water was evaporated to obtain 82 g of phosphate-modified dimethylpolysiloxane of the present invention. This dimethylpolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

This compound was analyzed by NMR and IR (KBr method). The results of NMR analysis are given below and the IR spectrum is presented in FIG. 3.

Figure 3:
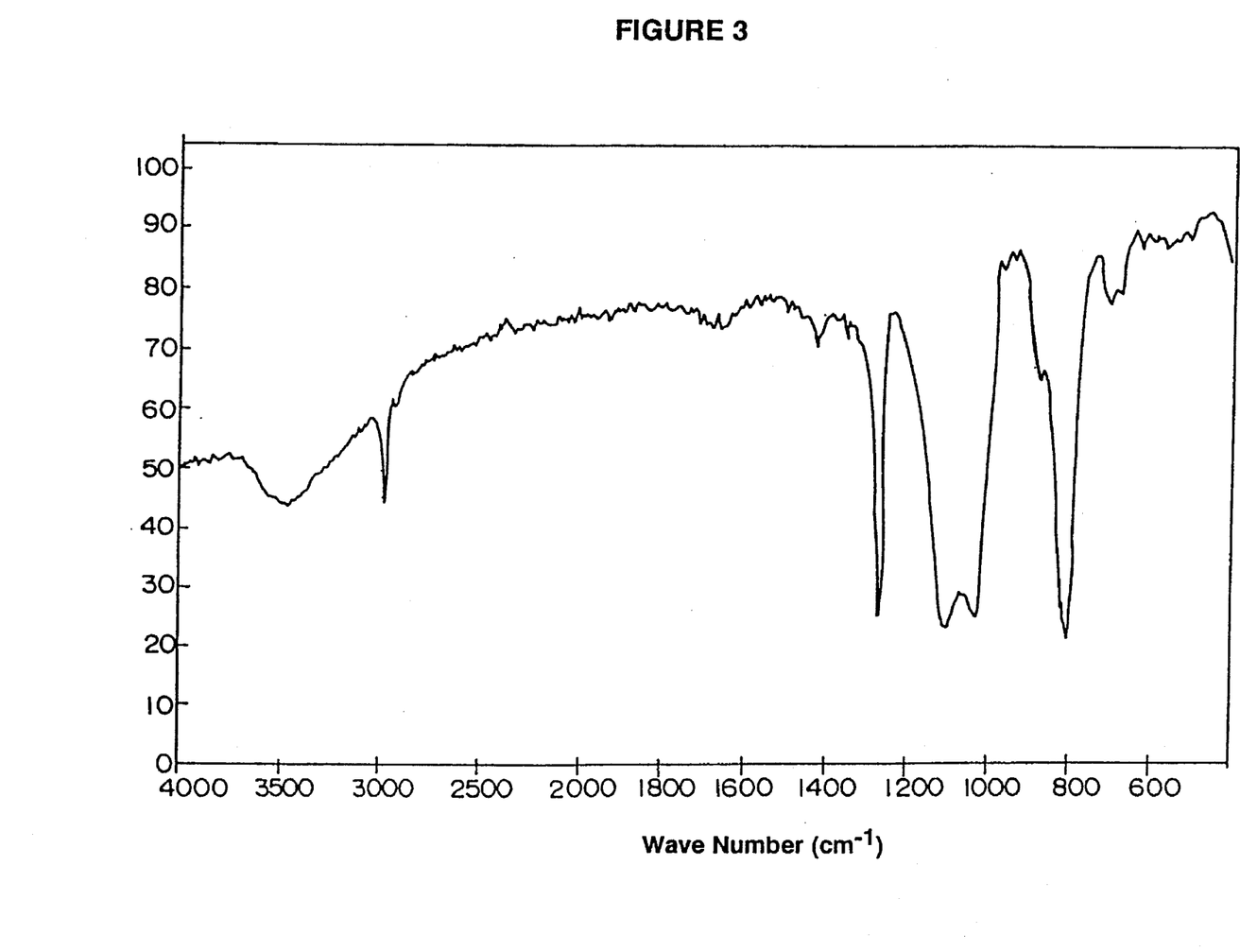
FIG. 3 is an IR spectrum of dimethylpolysiloxane prepared in Example 3.

$^{31}$P-NMR(CD$_3$OD+CDCl$_3$); δ(ppm) 8.0

$^{1}$H-NMR(CD$_3$OD+CDCl$_3$); δ(ppm) −0.2 (broad s, 246H, Si—CH$_3$), 0.35 (m, 4H, —O—Si—C$\underline{H_2}$—CH$_2$—CH$_2$—O—), 1.43 (m, 4H, —O—Si—CH$_2$C$\underline{H_2}$CH$_2$—O—), 3.28 (m, 4H, —C$\underline{H_2}$—O—CH$_2$CH$_2$O—P—), 3.44 (m, 4H, —CH$_2$O—C$\underline{H_2}$CH$_2$O—P—), 3.73 (m, 4H, —CH$_2$O—P—).

These analytical results confirmed that this phosphate-modified dimethylpolysiloxane has the structure defined by the following formula.

Comparative Example 1

To 100 g of a solution of alcohol-modified dimethylpolysiloxane (trademark: X-22-4015, manufactured by Shin-Etsu Chemical Co., Ltd.) represented by the following formula, (wherein s:t=26:1), was added 1.7 g of solid phosphorus pentoxide in portions. The mixture was gradually heated up to 70° C. and stirred for 1 hour while maintaining the temperature at 70° C. Then, the mixture was heated up to 100° C. and again stirred for 4 hours. After leaving the mixture to go down to room temperature, a 20% sodium hydroxide solution was added to neutralize the reaction mixture. $^{31}$P-NMR (CDCl$_3$+ethanol) was measured on the resulting product to confirm a signal reflecting an unreacted phosphorus at 2.4 ppm, a signal reflecting a phosphoric monoester at 1.4 ppm, a signal reflecting phosphoric diester at 1.0 ppm, and a signal reflecting a pyrophosphoric acid at −8.3 ppm. Further, from the measurement of $^1$H-NMR (CDCl$_3$) on this product after washing with water, the phosphorylation rate (phosphorylated —OH equivalent× 100/original —OH equivalent) was found to be less than 30%. This dimethylpolysiloxane exhibited a poor emulsification stability to silicone oils commonly used in cosmetic compositions in the temperature range of 0° to 50° C. It also exhibited inferior compatibility with polar solvents such as water, lower alcohols, and the like.

Comparative Example 2

50 g of the same alcohol-modified dimethylpolysiloxane of both-end type (trademark: X-22-160AS) used in Example 2 and 3.5 g of phosphorus pentoxide were used and processed in the same manner as in Comparative Example 1. As a result of $^{31}$P-NMR (CDCl$_3$) measurement on the formed product, the molar ratio of unreacted phosphoric acid:monoester:diester was confirmed to be 3:2:1. Neither emulsification stability nor compatibility of this dimethylpolysiloxane was satisfactory, as in the product of Comparative Example 1.

Example 4

A solution of 5.3 g of phosphorus oxychloride dissolved in 10 g of tetrahydrofuran was cooled to −30° C. To this solution, a solution of 70 g of alcohol-modified dimethylpolysiloxane used in Comparative Example 1 (trademark: X-22-4015) and 3.5 g of triethylamine dissolved in 30 g of tetrahydrofuran was added dropwise over 30 minutes, and reacted. The reaction mixture was left for aging for 4 hours, while maintaining the temperature of the reaction system below −20° C. Then, a solution of 7.0 g of sodium hydroxide dissolved in 15 g of ion-exchanged water was added dropwise to the reaction mixture over 30 minutes. The mixture was continuously stirred for 12 hours at 0° C. and the reaction was completed. Then, after removing the solvent by evaporation, the mixture was washed with ion-exchanged water (300 g×3). Water was evaporated to obtain 69 g of phosphate-modified dimethylpolysiloxane (phosphate conversion rate: greater than 95%). This phosphate-modified organopolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

This compound was analyzed by NMR and IR (KBr method). The results of NMR analysis are given below and the IR spectrum is presented in FIG. 4.

Figure 4:
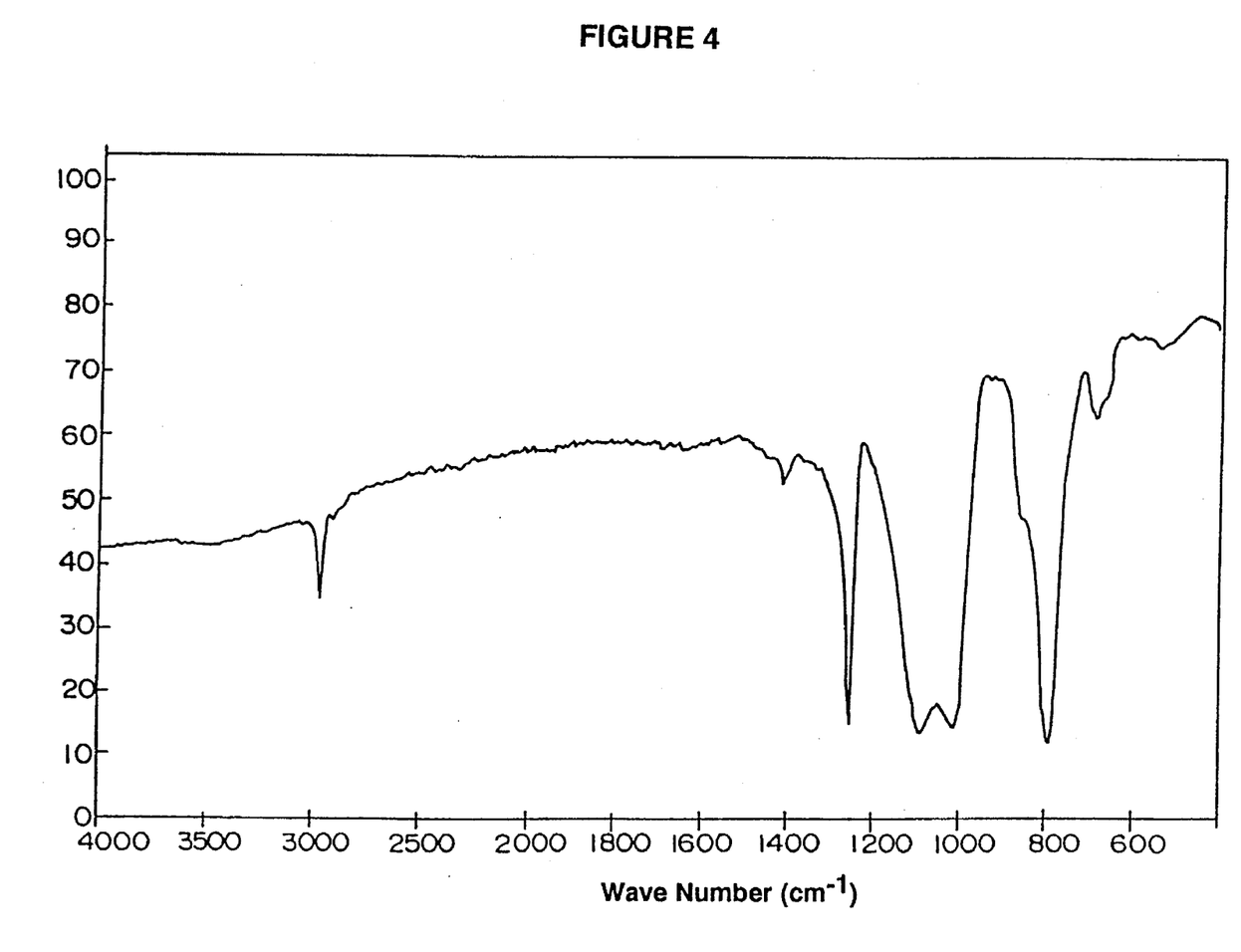
FIG. 4 is an IR spectrum of dimethylpolysiloxane prepared in Example 4.

$^{31}$P-NMR(CD$_3$OD+CDCl$_3$); δ(ppm) 7.87

$^1$H-NMR(CD$_3$OD+CDCl$_3$); δ(ppm) −0.10 (broad s, 155H, Si—CH$_3$), 0.33 (m, 2H, O—Si—$\underline{CH_2}$—CH$_2$), 1.46 (m, 2H, O—Si—CH$_2\underline{CH_2}$CH$_2$), 3.27 (m, 2H, —C$\underline{H_2}$—O—CH$_2$CH$_2$—O—P), 3.35, 3.44 (m, 2H, —CH$_2$OC$\underline{H_2}$CH$_2$O—P), 3.53, 3.73 (m, 2H, —$\underline{CH_2}$O—P—).

Example 5

A solution of 13.2 g of phosphorus oxychloride dissolved in 20 g of tetrahydrofuran was cooled to −30° C. To this solution, a solution of 28.2 g of one-end type alcohol-modified dimethylsiloxane synthesized by a known method (Japanese Patent Laid-open No. 195389/1987), represented by the above formula, and 8.7 g of triethylamine dissolved in 30 g of tetrahydrofuran was added dropwise over 20 minutes. The mixture was left for aging for 4 hours, while maintaining the temperature of the reaction system below −20° C. Then, a solution of 17.5 g of sodium hydroxide dissolved in 30 g of ion-exchanged water was added dropwise to the reaction mixture over 20 minutes. The mixture was continuously stirred for 12 hours at 0° C. and the reaction was completed. The reaction product was extracted from the reaction mixture by adding 70 g of ion-exchanged water, and further adding a mixed solvent of ether and ethanol. The organic layer was washed with ion-exchanged water, followed by removal of the water layer. The solvent was evaporated under a reduced pressure to obtain 32 g of phosphate-modified dimethylsiloxane of the present invention.

This phosphate-modified dimethylsiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

$^{31}$P-NMR(CDCl$_3$); δ(ppm) 8.0 $^1$H-NMR (CDCl$_3$); δ(ppm) −0.03 (—O—Si (CH$_3$)$_2$—CH$_2$—), −0.06 ((CH$_3$)$_3$Si—O), 0.5 (Si—C$\underline{H_2}$), 1.2 (—CH$_2$—(C$\underline{H_2}$)$_8$—CH$_2$—CH$_2$—O—P), 1.6 (—CH$_2$—CH$_2$—O—P), 3.8 (—$\underline{CH_2}$—O—P), IR; Si—O—Si 1050 cm$^{-1}$, Si—C 1245 cm$^{-1}$, 840 cm$^{-1}$.

Example 6

A solution of 5.5 g of phosphorus oxychloride dissolved in 20 g of tetrahydrofuran was cooled to −30° C. To this solution, a solution of 50.0 g of branched type alcohol-modified dimethylpolysiloxane synthesized by a known method (Japanese Patent Laid-open No. 195389/1987), represented by the above formula, and 3.7 g of triethylamine dissolved in 50 g of tetrahydrofuran was added dropwise over 30 minutes. The mixture was left for aging for 4 hours, while maintaining the temperature of the reaction system below −20° C. Then, a solution of 7.3 g of sodium hydroxide dissolved in 10 g of ion-exchanged water was added dropwise to the reaction mixture over 20 minutes. The mixture was continuously stirred for 12 hours at 0° C. and the reaction was completed. The reaction product was extracted from the reaction mixture by adding 100 g of ion-exchanged water and a mixed solvent of ether and ethanol. The organic layer was washed with ion-exchanged water, followed by removal of the water layer. The solvent was evaporated under reduced pressure to obtain 52 g of phosphate-modified dimethylpolysiloxane of the present invention.

This phosphate-modified dimethylpolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

$^{31}$P-NMR(CDCl$_3$); δ(ppm) 7.9 $^1$H-NMR(CDCl$_3$); δ(ppm) 0.1 (Si—C$\underline{H}_3$), 0.5 (Si—C$\underline{H}_2$), 1.3 (—CH$_2$—(C$\underline{H}_2$)$_8$—CH$_2$—CH$_2$—O—P), 1.7 (—C$\underline{H}_2$—CH$_2$—O—P), 3.9 (—C$\underline{H}_2$—O—P), IR; Si—O—Si 1020 cm$^{-1}$, Si—C 1260 cm$^{-1}$, 800 cm$^{-1}$.

Example 7

$$HO\text{-}\cdots\text{-}\underset{\underset{CH_3}{|}}{\overset{\overset{CH_3}{|}}{(Si-O)_{20}}}\text{-}\underset{\underset{CH_3}{|}}{\overset{\overset{CH_3}{|}}{Si}}\text{-}\cdots\text{-}OH + POCl_3 \longrightarrow \longrightarrow$$

$$NaO\text{-}\overset{\overset{O}{\|}}{\underset{\underset{ONa}{|}}{P}}\text{-}O\text{-}\cdots\text{-}\underset{\underset{CH_3}{|}}{\overset{\overset{CH_3}{|}}{(Si-O)_{20}}}\text{-}\underset{\underset{CH_3}{|}}{\overset{\overset{CH_3}{|}}{Si}}\text{-}\cdots\text{-}O\text{-}\overset{\overset{O}{\|}}{\underset{\underset{ONa}{|}}{P}}\text{-}ONa$$

A solution of 6.5 g of phosphorus oxychloride dissolved in 20 g of tetrahydrofuran was cooled to −30° C. To this solution, a solution of 40.0 g of both-end type alcohol-modified dimethylpolysiloxane synthesized by a known method (Japanese Patent Laid-open No. 195389/1987), represented by the above formula, and 4.3 g of triethylamine dissolved in 40 g of tetrahydrofuran was added dropwise over 30 minutes. The mixture was left for aging for 4 hours, while maintaining the temperature of the reaction system below −20° C. Then, a solution of 8.5 g of sodium hydroxide dissolved in 10 g of ion-exchanged water was added dropwise to the reaction mixture over 20 minutes. The mixture was continuously stirred for 12 hours at 0° C. and the reaction was completed. The reaction product was extracted from the reaction mixture by adding 100 g of ion-exchanged water and a mixed solvent of ether and ethanol. The organic layer was washed with ion-exchanged water, followed by removal of the water layer. The solvent was evaporated under reduced pressure to obtain 41 g of phosphate-modified dimethylpolysiloxane of the present invention.

This phosphate-modified dimethylpolysiloxane exhibited a stable emulsifying capability, irrespective of temperatures within the range of 0° to 50° C., to silicone oils commonly used in cosmetic compositions. It also exhibited excellent compatibility with polar solvents such as, water, lower alcohols, and the like.

$^{31}$P-NMR(CDCl$_3$); δ(ppm) 7.9 $^1$H-NMR(CDCl$_3$); δ(ppm) 0.1 (Si—C$\underline{H}_3$), 0.5 (Si—C$\underline{H}_2$), 1.2 (—CH$_2$—(C $H_2)_8$—$CH_2$—$CH_2$—O—P), 1.6 (—$CH_2$—$CH_2$—O—P), 3.8 (—$CH_2$—O—P), IR; Si—O—Si $\overline{1020}$ cm$^{-1}$, Si—C 1260 cm$^{-1}$, 800 cm$^{-1}$.

Example 8

A solution of 11.0 g of phosphorus oxychloride dissolved in 20 g of tetrahydrofuran was cooled to −30° C. To this solution, a solution of 50.0 g of alcohol-modified dimethylpolysiloxane (KF-355A; manufactured by Shin-Etsu Chemical Co., Ltd.) represented by the above formula, and 7.3 g of triethylamine dissolved in 25 g of tetrahydrofuran was added dropwise over 30 minutes. The mixture was left for aging for 4 hours, while maintaining the temperature of the reaction system below −20° C. Then, a solution of 14.7 g of sodium hydroxide dissolved in 20 g of ion-exchanged water was added dropwise to the reaction mixture over 20 minutes. The mixture was continuously stirred for 5 hours at 0° C. and the reaction was completed. The tetrahydrofuran layer was separated and the solvent was evaporated under a reduced pressure. The insoluble substances were removed by filtration by adding ethanol. The ethanol was evaporated under reduced pressure to obtain 57 g of phosphate-modified dimethylpolysiloxane of the present invention.

This phosphate-modified dimethylpolysiloxane exhibited a stable emulsifying capability, irrespective of temperatures within the range of 0° to 50° C., to silicone oils commonly used in cosmetic compositions. It also exhibited excellent compatibility with polar solvents such as, water, lower alcohols, and the like.

$^{31}$P-NMR(CDCl$_3$); δ(ppm) 7.8 $^1$H-NMR(CDCl$_3$); δ(ppm) 0.1 (Si—C$\underline{H_3}$), 0.5 (Si—C$\underline{H_2}$), 1.5 (Si—CH$_2$—C$\underline{H_2}$—CH$_2$—O), 3.4 (—O—C$\underline{H_2}$—), 3.9 (—C$\underline{H_2}$—O—P), IR; Si—O—Si 1025 cm$^{-1}$, Si—C 1270 cm$^{-1}$, 800 cm$^{-1}$.

Example 9

A solution of 11.6 g of phosphorus oxychloride dissolved in 30 g of tetrahydrofuran was cooled to −30° C. To this solution, a solution of 50.0 g of both-end type alcohol-modified dimethylpolysiloxane synthesized by a known method (Japanese Patent Laid-open No. 195389/1987), represented by the above formula, and 7.6 g of triethylamine dissolved in 40 g of tetrahydrofuran was added dropwise over 30 minutes. The mixture was left for aging for 4 hours, while maintaining the temperature of the reaction system below −20° C. Then, a solution of 15.1 g of sodium hydroxide dissolved in 20 g of ion-exchanged water was added dropwise to the reaction mixture over 20 minutes. The mixture was continuously stirred for 12 hours at 0° C. and the reaction was completed. The reaction product was extracted from the reaction mixture by adding 100 g of ion-exchanged water and a mixed solvent of ether and ethanol. The organic layer was washed with ion-exchanged water, followed by removal of the water layer. The solvent was evaporated under reduced pressure to obtain 52 g of phosphate-modified dimethylpolysiloxane of the present invention.

This phosphate-modified dimethylpolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

$^{31}$P-NMR(CDCl$_3$); δ(ppm) 7.9 $^1$H-NMR (CDCl$_3$); δ(ppm) 0.1 (Si—CH$_3$), 0.5 (Si—CH$_2$), 1.2 (—CH$_2$—(CH$_2$)$_8$—CH$_2$—CH$_2$—O—P), 1.6 (—CH$_2$—CH$_2$—O—P), 3.8 (—CH$_2$—O—P), IR; Si—O—Si $\overline{1020}$ cm$^{-1}$, Si—C $\overline{1260}$ cm$^{-1}$, 800 cm$^{-1}$.

Example 10

A solution of 23.7 g of phosphorus oxychloride dissolved in 30 g of tetrahydrofuran was cooled to −30° C. To this solution, a solution of 30.0 g of both-end type alcohol-modified dimethylpolysiloxane synthesized by a known method (Japanese Patent Laid-open No. 195389/1987), represented by the above formula, and 15.6 g of triethylamine dissolved in 40 g of tetrahydrofuran was added dropwise over 30 minutes. The mixture was left for aging for 4 hours, while maintaining the temperature of the reaction system below −20° C. Then, a solution of 30.9 g of sodium hydroxide dissolved in 40 g of ion-exchanged water was added dropwise to the reaction mixture over 20 minutes. The mixture was continuously stirred for 12 hours at 0° C. and the reaction was completed. The reaction product was extracted from the reaction mixture by adding 100 g of ion-exchanged water and a mixed solvent of ether and ethanol. The organic layer was washed with ion-exchanged water, followed by removal of the water layer. The solvent was evaporated under reduced pressure to obtain 42 g of phosphate-modified dimethylpolysiloxane of the present invention.

This phosphate-modified dimethylpolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

$^{31}$P-NMR(CDCl$_3$); δ(ppm) 8.0 $^1$H-NMR (CDCl$_3$); δ(ppm) 0.1 (Si—CH$_3$), 0.5 (Si—CH$_2$), 1.2 (—CH$_2$—(CH$_2$)$_8$—CH$_2$—CH$_2$—O—P), 1.6 (—CH$_2$—CH$_2$—O—P), 3.8 (—CH$_2$—O—P), IR; Si—O—Si $\overline{1020}$ cm$^{-1}$, Si—C $\overline{1260}$ cm$^{-1}$, 800 cm$^{-1}$.

Example 11

A solution of 20.1 g of phosphorus oxychloride dissolved in 30 g of tetrahydrofuran was cooled to −30° C. To this solution, a solution of 50.0 g of both-end type alcohol-modified dimethylpolysiloxane synthesized by a known method (Japanese Patent Laid-open No. 195389/1987), represented by the above formula, and 13.2 g of triethylamine dissolved in 40 g of tetrahydrofuran was added dropwise over 30 minutes. The mixture was left for aging for 4 hours, while maintaining the temperature of the reaction system below −20° C. Then, a solution of 26.2 g of sodium hydroxide dissolved in 40 g of ion-exchanged water was added dropwise to the reaction mixture over 20 minutes. The mixture was continuously stirred for 12 hours at 0° C. and the reaction was completed. The reaction product was extracted from the reaction mixture by adding 100 g of ion-exchanged water and a mixed solvent of ether and ethanol. The organic layer was washed with ion-exchanged water, followed by removal of the water layer. The solvent was evaporated under reduced pressure to obtain 52 g of phosphate-modified dimethylpolysiloxane of the present invention.

This phosphate-modified dimethylpolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

$^{31}$P-NMR(CDCl$_3$); δ(ppm) 7.9 $^1$H-NMR(CDCl$_3$); δ(ppm) 0.1 (Si—C$\underline{H_3}$), 0.5 (Si—C$\underline{H_2}$), 1.2 (—C$\underline{H_2}$—(CH$_2$)$_8$—CH$_2$—CH$_2$—O—P), 1.6 (—C$\underline{H_2}$—CH$_2$—O—P), 3.8 (—C$\underline{H_2}$—O—P), IR; Si—O—Si 1020 cm$^{-1}$, Si—C 1260 cm$^{-1}$, 800 cm$^{-1}$.

Example 12

A solution of 13.2 g of phosphorus oxychloride dissolved in 20 g of tetrahydrofuran was cooled to −30° C. To this solution, a solution of 30.0 g of one-end type alcohol-modified dimethylsiloxane synthesized by a known method (Japanese Patent Laid-open No. 195389/1987), represented by the above formula, and 8.7 g of triethylamine dissolved in 30 g of tetrahydrofuran was added dropwise over 20 minutes. The mixture was left for aging for 4 hours, while maintaining the temperature of the reaction system below −20° C. Then, a solution of 17.5 g of sodium hydroxide dissolved in 30 g of ion-exchanged water was added dropwise to the reaction mixture over 20 minutes. The mixture was continuously stirred for 12 hours at 0° C. and the reaction was completed. The reaction product was extracted from the reaction mixture by adding 70 g of ion-exchanged water and a mixed solvent of ether and ethanol. The organic layer was washed with ion-exchanged water, followed by removal of the water layer. The solvent was evaporated under reduced pressure to obtain 32 g of phosphate-modified dimethylsiloxane of the present invention.

This phosphate-modified dimethylsiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

$^{31}$P-NMR(CDCl$_3$); δ(ppm) 7.9 $^1$H-NMR( CDCl$_3$ ); δ(ppm) 0.03 (—O—Si (C$\underline{H_3}$)$_2$—CH$_2$—), 0.06 ((C

H$_3$)$_3$Si—O), 0.5 (Si—CH$_2$), 1.2 (—CH$_2$—(CH$_2$)$_5$—CH$_2$—CH$_2$—O—P), 1.5 (O—CH$_2$—CH$_2$), (—CH$_2$—CH$_2$—O—P), 3.3 (—O—CH$_2$), 3.9 (—CH$_2$—O—P), IR; Si—O—Si 1050 cm$^{-1}$, Si—C 1245 cm$^{-1}$, 840 cm$^{-1}$.

Test Example 1

Foaming capability of the above-described phosphate-modified dimethyl(poly)siloxanes were measured by the following method.

Measurement Method 100 ml of 1% aqueous solution of each compound was charged in a cylinder of 6.5 cm diameter, and subjected to reversal agitation at 1,000 rpm and allowed to stand still for 30 seconds. The height of the foam remained was then measured. The results are presented below.

85 mm

210 mm

244 mm

From the above results, it was made clear that the foaming capability can be promoted by introducing a longer chain alkyl group and by using a compound with a shorter silicon chain, i.e., (n) smaller than 10. In addition, the two compounds used in Comparative Examples, both of which did not fall in the group defined in the aforementioned formula (2), were found poor in the foaming capability.

Example 13

-continued

A solution of 5.4 g of phosphorus oxychloride dissolved in 10 g of tetrahydrofuran was cooled to −30° C. To this solution, a solution of 50.0 g of side chain type alcohol-modified dimethylpolysiloxane synthesized by a known method (Japanese Patent Laid-open No. 195389/1987), represented by the above formula, and 3.6 g of triethylamine dissolved in 40 g of tetrahydrofuran was added dropwise over 20 minutes. The mixture was left for aging for 4 hours, while maintaining the temperature of the reaction system below −20° C. Then, a solution of 7.1 g of sodium hydroxide dissolved in 15 g of ion-exchanged water was added dropwise to the reaction mixture over 20 minutes. The mixture was continuously stirred for 12 hours at 0° C. and the reaction was completed. The reaction product was extracted from the reaction mixture by adding 70 g of ion-exchanged water and a mixed solvent of ether and ethanol. The organic layer was washed with ion-exchanged water, followed by removal of the water layer. The solvent was evaporated under reduced pressure to obtain 51 g of phosphate-modified dimethylpolysiloxane of the present invention.

This phosphate-modified dimethylpolysiloxane exhibited a stable emulsifying capability, irrespective of temperatures within the range of 0° to 50° C., to silicone oils commonly used in cosmetic compositions. It also exhibited excellent compatibility with polar solvents such as water, lower alcohols, and the like.

$^{31}$P-NMR(CDCl$_3$); δ(ppm) 8.0 $^1$H-NMR(CDCl$_3$); δ(ppm) 0.0 (CH$_3$—Si—O), 0.4 (Si—CH$_2$), 1.2 (—CH$_2$—(CH$_2$)$_5$—$\overline{CH}_2$—CH$_2$—O—P), 1.5 ($\overline{O}$—CH$_2$—CH$_2$), (—C$\overline{H}_2$—CH$_2$—O—P), 3.4 (—O—CH$_2$), 4.0 (—C$\overline{H}_2$—O—P), IR; Si—O—Si 1020 cm$^{-1}$, Si—C 1265 cm$^{-1}$, $\overline{800}$ cm$^{-1}$.

Example 14

A solution of 7.9 g of phosphorus oxychloride dissolved in 15 g of tetrahydrofuran was cooled to −30° C. To this solution, a solution of 50.0 g of both-end type alcohol-modified dimethylpolysiloxane synthesized by a known method (Japanese Patent Laid-open No. 195389/1987), represented by the above formula, and 5.2 g of triethylamine dissolved in 40 g of tetrahydrofuran was added dropwise over 20 minutes. The mixture was left for aging for 4 hours, while maintaining the temperature of the reaction system below −20° C. Then, a solution of 10.3 g of sodium hydroxide dissolved in 20 g of ion-exchanged water was added dropwise to the reaction mixture over 20 minutes. The mixture was continuously stirred for 12 hours at 0° C. and the reaction was completed. The reaction product was extracted from the reaction mixture by adding 70 g of ion-exchanged water and a mixed solvent of ether and ethanol. The organic layer was washed with ion-exchanged water, followed by removal of the water layer. The solvent was evaporated under reduced pressure to obtain 52 g of phosphate-modified dimethylpolysiloxane of the present invention.

This phosphate-modified dimethylpolysiloxane exhibited a stable emulsifying capability, irrespective of temperatures within the range of 0° to 50° C., to the silicone oils commonly used in cosmetic compositions. It also exhibited excellent compatibility with polar solvents such as water, lower alcohols, and the like.

$^{31}$P-NMR(CDCl$_3$); δ(ppm) 8.0 $^1$H-NMR(CDCl$_3$); δ(ppm) −0.1 (CH$_3$—Si—O), 0.4 (Si—CH$_2$), 1.2 (—CH$_2$—(CH$_2$)$_5$—$\overline{CH}_2$—CH$_2$—O—P), 1.5 ($\overline{O}$—CH$_2$—CH$_2$), (—C$\overline{H}_2$—CH$_2$—O—P), 3.3 (—O—CH$_2$), 4.0 (—C$\overline{H}_2$—O—P), IR; Si—O—Si 1020 cm$^{-1}$, Si—C 1260 cm$^{-1}$, $\overline{800}$ cm$^{-1}$.

FIELD OF INDUSTRIAL APPLICATION

The phosphate-modified organo(poly)siloxanes of the present invention can stably emulsify silicone oils commonly used in cosmetic compositions, irrespective of temperatures, and exhibit excellent compatibility with polar components and good foaming capability. These characteristics make the phosphate-modified organo(poly)siloxanes of the present invention suitable for use as a component for toiletries, such as skin cosmetics, skin detergents, hair cosmetics, hair detergents, and the like. In addition, according to the process of the present invention, phosphates or the salts thereof can be easily introduced to the silicon atoms at any desired position of organo(poly)siloxanes to obtain phosphate-modified organo(poly)siloxanes.

We claim:

1. A phosphate-modified organo(poly) siloxane represented by the following formula (1):

(1)

wherein:

R, which may be the same or different, indicates an alkyl group or an alkoxy group having 1 to 22 carbon atoms, or a group represented by the following formula (2) or (3):

(2)

(3)

wherein $R^4$ and $R^6$ designate an alkylene group having 2 to 4 carbon atoms; $R^5$ indicates a linear or branched alkylene group having 9 to 50 carbon atoms, which may or may not contain hydroxy groups; $M^1$ and $M^2$ indicate a hydrogen atom, an alkali metal, an ammonium group, an alkyl amine or an alkanol amine; q is a number of 0 to 200; r is 0 or 1; and $R^1$ and $R^2$ designate a group represented by the following formula (2') or (3'):

(2')
   (3')

wherein $R^4$ and $R^6$ designate the same groups as defined above; $R^{5'}$ indicates a linear or branched alkylene group having 1 to 50 carbon atoms, which may or may not contain hydroxy groups; and q, r, $M^1$ and $M^2$ are the same as defined previously; or an alkyl group or an alkoxy group having 1 to 22 carbon atoms;

provided that at least one of $R^1$, $R^2$ or R represents the group indicated by the formula (2) or (2'); and n indicates a number of 0 to 1000.

2. The phosphate-modified organo(poly)siloxane according to claim 1, wherein $R^{5'}$ in the group represented by formula (2), (2'), (3), or (3') is an alkylene group having 4 to 15 carbon atoms.

3. The phosphate-modified organo(poly)siloxane according to claim 1, wherein $R^{5'}$ in the group represented by formula (2), (2'), (3), or (3') is an alkylene group having 6 to 12 carbon atoms.

4. The phosphate-modified organo(poly)siloxane according to claim 1, wherein q in the group represented by formula (2), (2'), (3), or (3') is a number of 0 to 15, and r is 0.

5. The phosphate-modified organo(poly)siloxane according to claim 1, wherein R in formula (1) is an alkyl group or an alkoxy group having 1 to 6 carbon atoms.

6. The phosphate-modified organo(poly)siloxane according to claim 1, wherein $R^5$ in the group represented by formula (2) or (3) is an alkylene group having 9 to 12 carbon atoms, provided that the one of R in formula (1) is a methyl group and the other is the group represented by formula (2) or (3).

7. The phosphate-modified organo(poly)siloxane according to claim 1, wherein n in formula (I) is a number of 0 to 100.

8. A phosphate-modified organo(poly)siloxane represented by the following formula (1):

(1)

wherein:

R, which may be the same or different, indicates an alkyl group or an alkoxy group having 1 to 22 carbon atoms; and $R^1$ and $R^2$ designate a group represented by the following formula (2') or (3'):

(2')
   (3')

wherein $R^4$ and $R^6$ designate an alkylene group having 2 to 4 carbon atoms; $R^{5'}$ indicates a linear or branched alkylene group having 1 to 50 carbon atoms; which may or may not contain hydroxy groups; $M^1$ and $M^2$ indicate a hydrogen atom, an alkali metal, an ammonium group, an alkyl amine or an alkanol amine; q is a number of 0 to 200; r is 0 or 1; or an alkyl group or an alkoxy group having 1 to 22 carbon atoms;

provided that at least either one of $R^1$ or $R^2$ represents the group indicated by formula (2'); and n indicates a number of 0 to 1000.

9. The phosphate-modified organo(poly)siloxane according to claim 8, wherein $R^{5'}$ in the group represented by formula (2') or (3') is an alkylene group having 4 to 15 carbon atoms.

10. The phosphate-modified organo(poly)siloxane according to claim 8, wherein $R^{5'}$ in the group represented by formula (2') or (3') is an alkylene group having 6 to 12 carbon atoms.

11. The phosphate-modified organo(poly)siloxane according to claim 8, wherein q in the group represented by formula (2') or (3') is a number of 0 to 15, and r is 0.

12. The phosphate-modified organo(poly)siloxane according to claim 8, wherein R in formula (1) is an alkyl group or an alkoxy group having 1 to 6 carbon atoms.

13. The phosphate-modified organo(poly)siloxane according to claim 8, wherein n is a number of 0 to 100.

14. A process for preparing an organo(poly) siloxane having at least one group represented by the following formula as a group bonding to the silicon atoms in the molecular chain;

(2')

wherein $R^4$, $R^{5'}$, $R^6$, q and r are the same as defined below; and $M^1$ and $M^2$ indicate a hydrogen atom, an alkali metal, an ammonium group, an alkyl amine or an alkanol amine; which comprises reacting an alcohol-modified organo(poly) siloxane having at least one group represented by formula $HO-(R^4O)_q-R^{5'}-OR^6)_r-$, wherein $R^4$ and $R^6$ represent an alkylene group having 2 to 4 carbon atoms; $R^{5'}$ indicates a linear or branched alkylene group having 1 to 50 carbon atoms, which may or may not contain hydroxy groups, q is a number of 0 to 200, and r is 0 or 1, as a group bonded to the silicon atoms in the molecular chain, with an oxyhalogenated phosphorus; and hydrolyzing the bonds between the phosphorus and the halogen.

15. The phosphate-modified organo(poly) siloxane according to claim 8, wherein R in formula (1) is a methyl group and $R^{5'}$ in the group represented by formula (2') or (3') is an alkylene group having 6 to 12 carbon atoms.

16. The process for preparing an organo(poly)siloxane according to claim 15, wherein the oxyhalogenated phosphorus compound is phosphorus oxychloride.

17. The phosphate-modified organo(poly)siloxane according to claim 1, wherein $R^5$ is a linear or branched alkylene group having 11 to 50 carbon atoms.

* * * * *

UNITED STATES PATENT AND TRADEMARK OFFICE
CERTIFICATE OF CORRECTION

PATENT NO. : 5,530,084

DATED : June 25, 1996

INVENTOR(S) : Takeshi IHARA, et al.

It is certified that error appears in the above-identified patent and that said Letters Patent is hereby corrected as shown below:

Column 27, lines 4-7 and

Column 2, lines 60-65, $$\text{``}M^1O-\underset{\underset{OM^2}{|}}{\overset{\overset{O}{\|}}{P}}-O-(R^4)_q-R^5-(OR^6)_r-\text{''} \quad \text{should read}$$

$$--M^1O-\underset{\underset{OM^2}{|}}{\overset{\overset{O}{\|}}{P}}-O-(R^4O)_q-R^5-(OR^6)_r---.$$

Column 10, line 6, "⁻P-NMR" should read --$^{31}$P-NMR. and

Column 12, line 19

Signed and Sealed this

Twenty-first Day of October 1997

Attest:

*Attesting Officer*

BRUCE LEHMAN

*Commissioner of Patents and Trademarks*